US009155697B2

(12) United States Patent  
Kim et al.

(10) Patent No.: US 9,155,697 B2
(45) Date of Patent: Oct. 13, 2015

(54) STABLE LIQUID COMPOSITIONS FOR TREATING STOMATITIS COMPRISING EPIDERMAL GROWTH FACTOR

(75) Inventors: Sun-Hee Kim, Cheongju (KR); Sang-Kil Lee, Suwon (KR); Chae-Ha Yoon, Yongin (KR); Sun-Mee Yang, Seoul (KR); Sang-Hyun Nam, Daejeon (KR); Kyeong-Sun Shin, Yongin (KR); Seung-Kook Park, Seoul (KR); Sang-Wook Lee, Seoul (KR)

(73) Assignee: DAEWOONG CO., LTD. (KR)

( * ) Notice: Subject to any disclaimer, the term of this patent is extended or adjusted under 35 U.S.C. 154(b) by 0 days.

(21) Appl. No.: 12/444,961

(22) PCT Filed: Oct. 9, 2007

(86) PCT No.: PCT/KR2007/004911
§ 371 (c)(1),
(2), (4) Date: Jun. 11, 2009

(87) PCT Pub. No.: WO2008/044852
PCT Pub. Date: Apr. 17, 2008

(65) Prior Publication Data
US 2010/0035809 A1 Feb. 11, 2010

(30) Foreign Application Priority Data
Oct. 9, 2006 (KR) .................. 10-2006-0097734

(51) Int. Cl.
*A61K 38/18* (2006.01)
*C07K 14/485* (2006.01)
*A61K 9/00* (2006.01)
*A61K 47/10* (2006.01)

(52) U.S. Cl.
CPC .............. *A61K 9/006* (2013.01); *A61K 38/1808* (2013.01); *A61K 47/10* (2013.01); *C07K 14/485* (2013.01)

(58) Field of Classification Search
None
See application file for complete search history.

(56) References Cited

U.S. PATENT DOCUMENTS

| | | | |
|---|---|---|---|
| 4,717,717 A | 1/1988 | Finkenaur | |
| 5,130,298 A * | 7/1992 | Cini et al. | 514/7.6 |
| 5,272,135 A * | 12/1993 | Takruri | 514/12 |
| 5,578,310 A | 11/1996 | M'Timkulu et al. | |
| 5,580,856 A | 12/1996 | Prestrelski et al. | |
| 5,705,485 A * | 1/1998 | Cini et al. | 514/8.2 |
| 6,180,601 B1 | 1/2001 | Jederstrom | |
| 6,288,113 B1 * | 9/2001 | Egi et al. | 514/530 |
| 6,458,387 B1 * | 10/2002 | Scott et al. | 424/489 |
| 2003/0060486 A1 | 3/2003 | Jacob et al. | |
| 2004/0063639 A1 | 4/2004 | Gentz et al. | |
| 2006/0128622 A1 * | 6/2006 | Treuheit et al. | 514/12 |
| 2008/0226724 A1 * | 9/2008 | Ji et al. | 424/486 |

FOREIGN PATENT DOCUMENTS

| | | | |
|---|---|---|---|
| CN | 1318415 A | 10/2001 | |
| EP | 0267015 A2 | 5/1988 | |
| EP | 0267015 A3 | 5/1988 | |
| EP | 0312208 A1 | 4/1989 | |
| JP | 63152324 A | 6/1988 | |
| JP | 5-505170 A | 8/1993 | |
| JP | 10182481 A | 7/1998 | |
| JP | 2002255852 A | 9/2002 | |
| JP | 2003-523399 A | 8/2003 | |
| JP | 2006517981 A | 8/2006 | |
| JP | 2006-249085 A | 9/2006 | |
| JP | 2008519012 A | 6/2008 | |
| KR | 1994-0023469 | 11/1994 | |
| KR | 1019960013439 B1 | 5/1996 | |
| KR | 2005-0055858 | 6/2005 | |
| WO | 90/12588 A1 | 11/1990 | |
| WO | 0056344 A1 | 9/2000 | |
| WO | WO-01-41821 | * | 6/2001 |
| WO | 01/62276 | 8/2001 | |
| WO | 01/62276 A1 | 8/2001 | |
| WO | 0217957 A1 | 3/2002 | |
| WO | 03/095637 | 11/2003 | |
| WO | 2004/028557 | 4/2004 | |
| WO | 2004082590 A2 | 9/2004 | |

(Continued)

OTHER PUBLICATIONS

Konturek et al., Role of epidermal growth factor in healing of chronic gastroduodenal ulcers in rats. Gastroenterology vol. 94:1300-1307 (1988).*
Sasaki et al. Keratinocyte growth factor and epidermal growth factor can reverse intestinal atrophy associated with elemental diets in mice. Experimal Physiology vol. 88/No. 2, pp. 261-267 (Mar. 2003).*
Oshitani, et al. "Clinical Evaluation of Sodium Alginate on Oral Mucositis Associated with Radiotherapy," J. Jpn. Soc. Cancer Ther., 25(6): 1129-1137, (1990). (Translation of Abstract Only).
Tanina, et al., "Stability and Therapeutical Efficacy of Allopurinol Gargle," Jpn. J. Hosp. Pharm., 18(5): 510-515, (1992). (Translation of Abstract Only).

(Continued)

Primary Examiner — Elizabeth C Kemmerer
Assistant Examiner — Regina M Deberry
(74) Attorney, Agent, or Firm — Cantor Colburn LLP

(57) ABSTRACT

Provided is a liquid composition for treating stomatitis, the liquid composition including: an epidermal growth factor; an adhesive polymer; and at least one stabilizer selected from the group consisting of ethylenediaminetetraacetic acid (EDTA) and salts thereof, histidine, lysine and inorganic acid salts thereof, arginin and inorganic acid salts thereof, and dextran. The liquid composition includes a stabilizer selected from EDTA (or salts thereof) and a certain amino acid (or inorganic acid salts thereof) and thus, physicochemical and biological stability of the epidermal growth factor can be substantially increased. Thus, the liquid composition can be stored and distributed for a long period of time. The stabilized composition includes an adhesive polymer, and thus, when ejected in a spray form in the mouth of a user, the liquid composition can be quickly attached to an inflammation site and exhibits effectiveness for a long period of time.

11 Claims, No Drawings

(56) References Cited

FOREIGN PATENT DOCUMENTS

| WO | 2006048501 A1 | 5/2006 |
|---|---|---|
| WO | 2006071840 A2 | 7/2006 |

OTHER PUBLICATIONS

Tamura, et al., "Evaluation of Sodium Polyacrylate as the Dispersion Agent to Prepare Allopurinol Gargle," Div. of Pharm., Niigata Univ. Med. Hosp., 55(1), (1995). (Translation of Abstract Only).

Epstein, J. B. et al., "The Correlation Between Epidermal Growth Factor Levels in Saliva and the Severity of Oral Mucositis During Oropharyngeal Radiation Therapy", Am. Cancer Society, 2000, vol. 89 (11): 2258-2265.

Japanese Office Action issued Dec. 27, 2011 for Application No. JP 2009-532289.

EP Extended Search Report dated Oct. 1, 2012 for Application No. 07833222.8-2112.

Japanese Office Action issued Sep. 11, 2012 for Application No. JP 2009-532289.

Lee, K.K. et al., Recombinant Human Epidermal Growth Factor Accelerates Recovery of Mouse Small Intestinal Mucosa After Radiation Damage, Int J Radiat Oncol Biol Phys. 2008; 71(4):1230-1235.

Wu, H.G. et al., Therapeutic effect of recombinant human epidermal growth factor (RhEGF) on mucositis in patients undergoing radiotherapy, with or without chemotherapy, for head and neck cancer: A double-blind placebo-controlled prospective phase 2 multi-institutional clinical trial, Cancer. 2009;115(16): 3699-3708. Doi: 10.1002/cncr.24414.

* cited by examiner

STABLE LIQUID COMPOSITIONS FOR TREATING STOMATITIS COMPRISING EPIDERMAL GROWTH FACTOR

TECHNICAL FIELD

The present invention relates to stable liquid compositions for treating stomatitis including an epidermal growth factor.

BACKGROUND ART

Stomatitis is a disease that affects oral mucosa. Specifically, stomatitis is an inflammation which is caused or exacerbated by pharmaceutical treatment, specifically by a chemotherapeutic or radioactive treatment, and in some cases, is accompanied by an ulcer(s). Stomatitis exhibits mild to severe symptoms. Patients suffering from severe stomatitis cannot eat food through their mouth. Meanwhile, erythematous mucositis, which is a type of stomatitis, appears within three days, more commonly within 5-7 days after exposure to a chemotherapeutic or radioactive treatment. Erythematous mucositis can progress to an ulcerative mucositis within 7 days after exposure to a chemotherapeutic treatment in general and some erythematous mucositises can progress to such a serious level that any drug treatment should be stopped.

Among patients who are treated with chemotherapy, a large number of patients suffer from mucositis although the severity thereof may differ. So, there is a great need to develop an effective and simple method for treating stomatitis. Conventionally, stomatitis is treated by oral cleansing or administration with various kinds of vitamins. Specifically, stomatitis caused by a chemotherapeutic or radioactive treatment can be treated by mouth wash administration of allopurinol or sodium alginate (Archives, Vol. 55, No. 1:28, 1995; Japanese Journal of Hospital Pharmacy, Vol. 18, No. 5:510, 1992; Japanese Journal of Nursing Acts, Vol. 37, No. 15:44, 1991; The Journal of Japanese Society for Cancer Therapy, Vol. 25, No. 6:1129, 1990). However, such a mouth wash administration shows low effectiveness in alleviating symptoms, is ineffective for serious stomatitis, and requires a long administration period to obtain any improvement in symptoms. Due to these problems, there have been many efforts to develop a drug or method for treating stomatitis which shows a high curative effect in a short period of time.

Most conventional compositions for treating stomatitis are prepared in ointments or patches which contain an adhesive polymer. For example, U.S. Pat. No. 56,578,310 discloses a bioadhesive ointment formed of an emulsion containing mineral oil, hydroxyl propyl methyl cellulose, and the like; and Korean Patent Application Pub. No. 1994-0023469 discloses plasters having a double film structure containing a steroid drug and a method of preparing the same.

As for other forms excluding ointments or patches, US Patent Application Pub. No. 2002/0219634 discloses a bioadhesvie solution or suspension having a viscosity ranging from 50-50,000 cps, and Korean Patent Application Pub. No. 2005-55858 discloses a drug delivery system for oral cavity in the form of a liquid or gel drug including a mixture of a hydrophilic polymer and a water-insoluble polymer.

Meanwhile, International Publication No. WO 03/95637 discloses use of an epidermal growth factor for treating stomatitis. The epidermal growth factor which is known as urogastrones is a polypeptide having a molecular weight of 6045 with 53 amino acids and three disulfide bonds. The epidermal growth factor stimulates mitosis and cell growth of various kinds of cells, such as an epithelial cell or a mesenchymal cell, and hinders gastric acid secretory, and thus, the epidermal growth factor is effective in treating a gastric ulcer or a wound on skin or a cornea (Carpenter, Experimental Cell Research, 164:1-10, 1986). Accordingly, if the epidermal growth factor is formulated together with an adhesive polymer, such as hydroxypropyl methyl cellulose, high effectiveness in treating stomatitis can be obtained.

This method, however, is inconvenient and can cause a second infection because ointments or patches which contain the epidermal growth factor and the adhesive polymer should be directly applied or attached to an oral inflammation or a wound by a patient. To avoid these problems, the epidermal growth factor and the adhesive polymer can be prepared in a liquid type and then formulated in a spray form. The liquid formulation method, however, decreases stability of the epidermal growth factor due to use of an aqueous medium in which molecules move relatively more actively.

DETAILED DESCRIPTION OF THE INVENTION

Technical Problem

Inventors of the present application found that a liquid formulation having high stability can be prepared using a stabilizer selected from the group consisting of ethylenediaminetetraacetic acid (EDTA), which is a conventional antioxidant, salts thereof, dextran, and certain amino acids.

The present invention provides a stable liquid composition for treating stomatitis including: a stabilizer selected from EDTA and salts thereof, dextran, and certain amino acids; an epidermal growth factor; and an adhesive polymer.

The present invention also provides a spray for treating stomatitis including the liquid composition.

Technical Solution

According to an aspect of the present invention, there is provided a liquid composition for treating stomatitis: including an epidermal growth factor; an adhesive polymer; and at least one stabilizer selected from the group consisting of ethylenediaminetetraacetic acid (EDTA) and salts thereof, histidine, lysine and inorganic acid salts thereof, arginin and inorganic acid salts thereof, and dextran.

According to another aspect of the present invention, there is provided a spray for treating stomatitis including the liquid composition.

The present invention will be described in detail.

In the present specification, the term 'stomatitis' is an inflammation which affects oral mucosa, can be caused or exacerbated by a pharmaceutical treatment, specifically by a chemotherapeutic or radioactive treatment, and can be accompanied by an ulcer. Stomatitis may exhibit from mild to such severe symptoms that patients suffering from stomatitis cannot eat food through their mouth.

The liquid composition according to the present invention includes a stabilizer selected from EDTA and salts thereof and a certain amino acid and inorganic acid salts thereof, and thus, physicochemical and biological stabilities of an epidermal growth factor can be significantly improved. Therefore, the liquid composition can be stored or distributed for a long period of time. The liquid composition includes an adhesive polymer and thus, when the liquid composition is ejected in a spray form into the mouth of a user, the liquid composition can be quickly attached to an inflammation site and can exhibit a pharmaceutical effect for a long period of time.

The liquid composition according to the present invention includes an epidermal growth factor acting as an active component. The epidermal growth factor can be a natural or recombinant protein in an amount which is therapeutically effective. That is, when the liquid composition is formulated in a unit form, for example, in a spray form, the amount of the epidermal growth factor may be in the range from about 0.1 to 1,000 µg/mL, preferably from 0.5 to 500 µg/mL, and more preferably 1.0 to 100 µg/mL. A liquid composition prepared to be formulated into a specific dosage form may include the epidermal growth factor in an amount ranging from 0.0001 to 0.01 w/v % based on the total amount of the liquid composition.

The liquid composition according to the present invention includes at least one stabilizer selected from the group consisting of: EDTA and salts thereof, such as disodium salt, calcium diodium salt, or trisodium salt; histidine; lysine and inorganic acid salts thereof, such as hydrochloride salt of lysine; arginin and inorganic acid salts thereof, such as a hydrochloride salt of arginin; and dextran. The sterilizer can be EDTA disodium salt, L-histidine, L-lysine hydrochlorate salt, L-arginin hydrochloride salt, and/or dextran having an average molecular weight ranging from 40,000 to 100,000 Da. Preferably, the stabilizer can include at least one selected from the group consisting of histidine, lysine, and arginin. For example, the stabilizer can include EDTA disodium salt and/or L-histidine.

The amount of the stabilizer present in the liquid composition may differ according to the kind of the stabilizer used. For example, the amount of the stabilizer may be in the range from 0.01 to 10 w/v %, specifically 0.05 to 5 w/v %, based on the total amount of the liquid composition. When the amount of the stabilizer is less than 0.01 w/v %, stabilization of the epidermal growth factor may not be achieved. On the other hand, when the amount of the stabilizer is greater than 10 w/v %, stability of the epidermal growth factor may be rather decreased.

The liquid composition according to the present invention includes the adhesive polymer and thus the liquid composition can be quickly attached to the inflammation site when applied into the oral cavity, and a sufficient viscosity can be maintained constant. The adhesive polymer can be celluloses, such as hydroxypropyl methyl cellulose, hydroxypropyl cellulose, hydroxyethyl cellulose, or sodium carboxymethyl cellulose; a hydrophilic polymer, such as sodium hyaluronate, carbomer (for example, Carbopol 940™ (ISP, USA)), xanthan gum, gellan gum, pullulan, pectin, or starches (for example, corn starch); a non-ionic surfactant, such as a copolymer of polyoxyethylene and polyoxypropylene; or a combination of these. The adhesive polymer can be a copolymer of polyoxyethylene and polyoxypropylene in a weight average molecular weight from 7,000 to 15,000, such as poloxamer 407™ (BASF, USA), or poloxamer 188™ (BASF, USA).

The amount of the adhesive polymer present in the liquid composition according to the present invention may differ according to the kind of the polymer used. The amount of the adhesive polymer may be in the range from 0.01 to 20 w/v %, specifically from 0.1 to 10 w/v %, based on the total amount of the liquid composition. When the amount of the adhesive polymer is less than 0.01 w/v %, the viscosity of the formulation is low and the adhesive effect is low. On the other hand, when the amount of the adhesive polymer is greater than 20 w/v %, the viscosity of the formulation is high and thus, it may be difficult to prepare or formulate the liquid composition into, for example, a spray form.

The viscosity of the liquid composition may be in the range from 50 to 10,000 cps, and specifically from 500 to 5,000 cps (mPas). When the viscosity of the liquid composition is less than 50 cps, the viscosity of the liquid composition may too low and thus, the liquid composition does not remain in a wound site and may directly flow to an esophagus. On the other hand, when the viscosity of the liquid composition is greater than 10,000 cps, the viscosity of the liquid composition may be too high, and thus, the liquid composition formulated into a spray form cannot be ejected.

The liquid composition according to the present invention may include a pharmaceutically acceptable carrier. For example, the liquid composition can include an aqueous medium, such as water, purified water, or water for injection. In some cases, the liquid composition may further include a pH controller, a preservative, a sweetening agent, or a flavouring agent. In consideration of stability of the epidermal growth factor included as an active component in the liquid composition according to the present invention, pH of the liquid composition may be in the range from 5 to 8, and specifically from 6 to 7. The pH controller which controls the pH of the liquid composition can be a buffer solution containing sodium phosphate monobasic, sodium phosphate bibasic, or sodium citrate. The preservative can be methylparaben, propylparaben, benzylalcohol, or sodium benzoate. The amounts of the pH controller, the preservative, the sweetening agent, and the flavouring agent may be appropriately controlled by one of ordinary skill in the art. For example, the amount of the preservative, such as methylparaben or propylparaben, may be in the range from 0.01 to 1.0 w/v % based on the total amount of the liquid composition, but is not limited thereto.

The liquid composition according to the present invention can be formulated in various kinds of forms suitable for oral cavity administration, specifically in a spray form. That is, the present invention provides a spray for treating stomatitis including the liquid composition. The spray can be of an aerosol form, a pump spray form, or a reconstitution spray form. The pumping spray from and the reconstitution spray form can prevent a decrease in stability of an active component caused by a propellant.

The pump spray form refers to a type of ejecting a drug solution, that is, a liquid composition according to the present invention, contained in a vessel to which a negative pressure is applied by pumping.

The reconstitution spray refers to a type of administrating a mixture of a solvent unit (that is, an adhesive excipient solution) and a primary component unit (that is, a liquid mixture composition of a human growth hormone and a stabilizer), in which when not used, the solvent unit is separated from the primary component unit. For example, according to an embodiment of the present invention, the spray used in the present invention can be a reconstitution spray which includes a solvent unit including an adhesive polymer and a primary component unit including an epidermal growth factor and a stabilizer, in which the solvent unit and the primary component unit are contained in different vessels from each other.

Advantageous Effects

A liquid composition according to the present invention includes a stabilizer selected from EDTA (or salts thereof), dextran, and certain amino acids (or inorganic acid salts thereof) and thus, physicochemical and biological stabilities of an epidermal growth factor can be substantially increased. Thus, the liquid composition can be stored and distributed for a long period of time. The stabilized composition includes an adhesive polymer, and thus, when ejected in a spray form in the mouth of a user, the liquid composition can be quickly attached to an inflammation site and exhibits effectiveness for a long period of time.

Best Mode

The present invention will be described in further detail with reference to the following examples. These examples are for illustrative purposes only and are not intended to limit the scope of the present invention.

Examples 1-5 and Comparative Example 1

Liquid compositions were prepared according to the components and amounts shown in Table 1. In Table 1, the amount of each component is represented by w/v %. A buffer (sodium phosphate monobasic) and sodium chloride were dissolved using refined water, and then a pH controller (phosphoric acid) was added thereto in an appropriate amount to adjust the pH to a range from 6 to 7. The resultant solution was heated to 80° C. in order to dissolve a preservative (methylparaben), and then the heated solution was mixed with an adhesive polymer poloxamer 407™ (BASF, USA). The mixture was stirred until a homogeneous mixture was obtained. A stabilizer (EDTA disodium salt, L-histidine, hydrochloric acid L-arginin, L-lysine hydrochloride, or dextran 70) and an epidermal growth factor were dissolved in the homogeneous mixture and water was added thereto until the final volume of the liquid composition reached 1 L. As Comparative Example, a liquid composition was prepared in the same manner as the method described above, except that no stabilizer was added.

Test Example 1

Stability Test Against Thermal Stress

The liquid compositions prepared according to Examples 1-5 and Comparative Example 1 were let to sit at 40° C. in a relative humidity of 75% for 4 weeks. Then, the amount and activity of the epidermal growth factor were measured. The amount was measured using a reverse phase HPLC, and the activity was measured using ELISA. The obtained values are denoted as a percentage (%) with respect to initial values.

The results are shown in Table 2.

TABLE 2

|  | Example 1 | Example 2 | Example 3 | Example 4 | Example 5 | Comparative Example 1 |
|---|---|---|---|---|---|---|
| Amount % | 89 | 90 | 85 | 86 | 84 | 52 |
| Activity % | 90 | 92 | 87 | 85 | 84 | 60 |

As shown in Table 2, the liquid compositions according to the present invention show high stability with respect to thermal stress. Specifically, when the liquid composition is prepared using EDTA or L-histidine which is used as an antioxidant, the liquid composition shows much higher stability.

Test Example 2

Stability Test against Physical Stress

To identify physical stability of an epidermal growth factor with respect to an external physical stress, the liquid compositions prepared according to Examples 1-5 and Comparative Example 1 were stirred for 3 hours at 200 rpm and the generated agglutination was identified. The amount of the epidermal growth factor in each liquid composition was quantified after the generated agglutinate was removed (0.45 µm syringe filter, Millipore). The obtained values are denoted as a percentage (%) with respect to initial values. The results are shown in Table 3.

TABLE 1

|  |  | Example 1 | Example 2 | Example 3 | Example 4 | Example 5 | Comparative Example 1 |
|---|---|---|---|---|---|---|---|
| Active Component | Epidermal growth factor | 0.005 | 0.005 | 0.005 | 0.005 | 0.005 | 0.005 |
| Buffer solution | Sodium phosphate monobasic | 0.36 | 0.36 | 0.36 | 0.36 | 0.36 | 0.36 |
| Isotonic agent | Sodium chloride | 0.87 | 0.87 | 0.87 | 0.87 | 0.87 | 0.87 |
| Preservative | Methyl paraben | 0.1 | 0.1 | 0.1 | 0.1 | 0.1 | 0.1 |
| Adhesive polymer (thickener) | Poloxamer 407 | 6 | 6 | 6 | 6 | 6 | 6 |
| Stabilizer | EDTA disodium salt | 0.5 |  |  |  |  |  |
|  | L-histidine |  | 1 |  |  |  |  |
|  | L-arginin hydrochloride |  |  | 1 |  |  |  |
|  | L-lysine hydrochloride |  |  |  | 1 |  |  |
|  | Dextran 70 |  |  |  |  | 0.1 |  |
| Aqueous medium | Refined water | Appropriate amount | Appropriate amount | Appropriate amount | Appropriate amount | Appropriate amount | Appropriate amount |
| Viscosity (cps) |  | 500-700 | | | | | |

TABLE 3

|  | Example 1 | Example 2 | Example 3 | Example 4 | Example 5 | Comparative Example 1 |
|---|---|---|---|---|---|---|
| Image | Clean and Transparent | Clean and Transparent | Trace amount of agglutination forms (three to four particles) | Trace amount of agglutination forms (one to three particles) | Clean and Transparent | Non-transparent |
| Amount after filtering % | 100.0 | 100.0 | 97.2 | 98.1 | 99.9 | 35.9 |

As shown in Table 3, the liquid compositions according to the present invention show excellent stability with respect to a physical stress.

Examples 6-11

Liquid compositions were prepared according to the components and amounts shown in Table 4 in the same manner as in Examples 1-5. In Table 4, the amount of each component is represented by w/v %.

TABLE 4

|  |  | Example 6 | Example 7 | Example 8 | Example 9 | Example 10 | Example 11 |
|---|---|---|---|---|---|---|---|
| Active Component | Epidermal growth factor | 0.005 | 0.005 | 0.005 | 0.005 | 0.005 | 0.005 |
| Buffer solution | Sodium phosphate monobasic | 0.36 | 0.36 | 0.36 | 0.36 | 0.36 | 0.36 |
| Isotonic agent | Sodium chloride | 0.87 | 0.87 | 0.87 | 0.87 | 0.87 | 0.87 |
| Preservative | Methyl paraben | 0.1 | 0.1 | 0.1 | 0.1 | 0.1 | 0.1 |
| Stabilizer | EDTA disodium salt | 0.5 | 0.5 | 0.5 | 0.5 | 0.5 | 0.5 |
| Adhesive polymer | Poloxamer 407 | 10 |  |  |  |  |  |
|  | Hydroxypropyl methyl cellulose 50 cps |  | 1 |  |  |  |  |
|  | Sodium hyaluronate |  |  | 0.1 |  |  |  |
|  | Xanthan gum |  |  |  | 0.2 |  |  |
|  | Carbomer 940 |  |  |  |  | 0.5 |  |
|  | Sodium carboxymethyl cellulose |  |  |  |  |  | 1.5 |
| Aqueous medium | Refined water | Appropriate | Appropriate | Appropriate | Appropriate | Appropriate | Appropriate |
| Viscosity (cps) |  | 1500-2000 |  |  |  |  |  |

Test Example 3

Sensory Test

A sensory test was performed using the liquid compositions prepared according to Examples 6-11 and Comparative Example 1. Since patients suffering from serious stomatitis cannot eat food, a drug for treating stomatitis should not be simulative to oral mucous membrane and when the drug is applied to an oral carvity, a great amount of the drug should remain at a lesion. 35 patients suffering from stomatitis were grouped by 5 patients. Each liquid composition was applied to an inflammation site in oral cavity of each group. After 1 hour after the application, a feeling of use in consideration of a feeling of wearing and a stimulus of a tongue was questioned. The results are shown in Table 5. The values shown in Table 5 are means of the feelings of patients.

TABLE 5

|  | Example 6 | Example 7 | Example 8 | Example 9 | Example 10 | Example 11 | Comparative Example 1 |
|---|---|---|---|---|---|---|---|
| Feeling of Use | 7.5 | 10.0 | 9.5 | 9.5 | 9.0 | 10.0 | 7.0 |
| Feeling of Wearing | 7.0 | 9.0 | 9.5 | 8.0 | 9.0 | 8.5 | 2.0 |

TABLE 5-continued

|  | Example 6 | Example 7 | Example 8 | Example 9 | Example 10 | Example 11 | Comparative Example 1 |
|---|---|---|---|---|---|---|---|
| Others | bitter and acrid tastes | None | None | None | A bit bitter Taste | None | bitter and acrid Tastes |

Feeling of Use: from 10 (excellent, no stimulus) to 1 (bad, stimulus and painful)
Feeling of Wearing: from 10 (most of the drug used remains in the lesion) to 1 (most of the drug used flows to the esophagus)

Feeling of Use: from 10 (excellent, no stimulus) to 1 (bad, stimulus and painful)
Feeling of Wearing: from 10 (most of the drug used remains in the lesion) to 1 (most of the drug used flows to the esophagus)

As shown in Table 5, the liquid compositions according to the present invention show a good feeling of use. Specifically, when a liquid composition is prepared using a cellulose-based expicient, better feeling of use could be obtained.

Examples 12-16

Liquid compositions were prepared according to the components and amounts shown in Table 6 in the same manner as in Examples 1-5. In Table 6, the amount of each component is represented by w/v %.

TABLE 6

|  |  | Example 12 | Example 13 | Example 14 | Example 15 | Example 16 |
|---|---|---|---|---|---|---|
| Active Component | Epidermal growth factor | 0.005 | 0.005 | 0.005 | 0.005 | 0.005 |
| Buffer solution | sodium phosphate monobasic | 0.36 | 0.36 | 0.36 | 0.36 | 0.36 |
| Isotonic agent | Sodium chloride | 0.87 | 0.87 | 0.87 | 0.87 | 0.87 |
| Preservative | Methyl paraben | 0.1 | 0.1 | 0.1 | 0.1 | 0.1 |
| Stabilizer | EDTA disodium salt |  |  | 0.5 |  |  |
|  | L-histidine |  | 1.0 |  | 1.0 | 1.0 |
| Adhesive polymer (thickener) | Poloxamer 407 | 6 | 9 | 9 |  |  |
|  | Hydroxypropyl methyl cellulose 50 cps |  |  |  | 1 |  |
|  | Sodium carboxymethyl cellulose |  |  |  |  | 1.5 |
| Aqueous medium | Refined water | Appropriate amount | Appropriate amount | Appropriate amount | Appropriate amount | Appropriate amount |
| Viscosity (cps) |  | 500-700 |  | 1200-1500 |  |  |

Test Example 4

Test for Room-temperature Stability

The liquid compositions prepared according to Examples 12-16 were let to sit at 25° C. in a relative humidity of 60% for 3 months. Then, the amount and activity of the epidermal growth factor were measured. The amount was measured using a reverse phase HPLC, and the activity was measured using ELISA. The obtained values are denoted as a percentage (%) with respect to initial values. The results are shown in Table 7.

TABLE 7

|  | Example 12 | Example 13 | Example 14 | Example 15 | Example 16 |
|---|---|---|---|---|---|
| Amount % | 90.2 | 100.0 | 99.2 | 99.4 | 98.4 |
| Activity % | 89.3 | 99.1 | 98.3 | 100.5 | 99.1 |

As shown in Table 7, the liquid compositions according to the present invention show excellent stability for three months at room temperature.

The invention claimed is:

1. A liquid pharmaceutical composition, comprising 0.0001 to 0.01 w/v % of an epidermal growth factor; 0.1 to 1.5 w/v % of an adhesive polymer selected from hydroxypropyl methyl cellulose, sodium carboxymethyl cellulose, sodium hyaluronic acid, or xanthan gum; and 0.5 to 1.0 w/v % of EDTA disodium salt,
   wherein w/v % concentration is based on the total amount of the liquid pharmaceutical composition,
   wherein the viscosity of the liquid pharmaceutical composition is in the range of 1500 to 2000 cps.

2. The liquid pharmaceutical composition of claim 1, wherein the stabilizer is 0.5 w/v % EDTA disodium salt.

3. A spray for treating stomatitis comprising the liquid pharmaceutical composition of claim 2.

4. The liquid pharmaceutical composition of claim 1, wherein the adhesive polymer is 1.0-1.5 w/v % of hydroxypropyl methyl cellulose.

5. A spray for treating stomatitis comprising the liquid pharmaceutical composition of claim 4.

6. The liquid pharmaceutical composition of claim 1, wherein the amount of the epidermal growth factor is 0.005 w/v % based on the total amount of the liquid composition.

7. A spray for treating stomatitis comprising the liquid pharmaceutical composition of claim 1.

8. The spray of claim 7, wherein the spray is a reconstitution spray comprising:
   a solvent unit comprising an adhesive polymer; and
   a primary component unit comprising an epidermal growth factor and a stabilizer,
   wherein the solvent unit and the primary component unit are contained in different vessels from each other.

9. A method for treating stomatitis comprising
   applying the liquid pharmaceutical composition of claim 1 to an oral inflammation site of a subject with stomatitis.

10. The method of claim 9, wherein the liquid pharmaceutical composition is in the form of a spray.

11. The liquid pharmaceutical composition of claim 1, comprising
   0.005 w/v % epidermal growth factor, and
   wherein the stabilizer is 0.5 w/v % EDTA disodium salt and the adhesive polymer is 1.0-1.5 w/v % of hydroxypropyl methyl cellulose or sodium carboxymethyl cellulose.

* * * * *